United States Patent [19]

Senyei et al.

[11] 4,357,259
[45] Nov. 2, 1982

[54] METHOD OF INCORPORATING WATER-SOLUBLE HEAT-SENSITIVE THERAPEUTIC AGENTS IN ALBUMIN MICROSPHERES

[75] Inventors: Andrew E. Senyei; Kenneth J. Widder, both of Chicago, Ill.

[73] Assignee: Northwestern University, Evanston, Ill.

[21] Appl. No.: 859,842

[22] Filed: Dec. 12, 1977

Related U.S. Application Data

[63] Continuation-in-part of Ser. No. 820,812, Aug. 1, 1977, abandoned.

[51] Int. Cl.$^3$ .................. B01J 13/02; A01N 25/28; A61K 9/64
[52] U.S. Cl. .................. 252/316; 252/62.53; 252/62.54; 424/1; 424/22; 424/36; 424/181; 427/338
[58] Field of Search .................. 252/316; 424/22, 36; 427/338; 106/135

[56] References Cited

U.S. PATENT DOCUMENTS

| | | | |
|---|---|---|---|
| 2,989,417 | 6/1961 | Overman | 106/135 X |
| 3,137,631 | 6/1964 | Soloway | 424/36 X |
| 3,474,777 | 10/1969 | Figge et al. | 424/19 X |
| 3,663,687 | 5/1972 | Evans | 264/0.5 X |
| 3,937,668 | 2/1976 | Zolle | 252/316 |

OTHER PUBLICATIONS

Kramer: J. Pharm. Sci., 63, 1646–1647 (1974).
Zolle et al.: Int. J. Appl. Radiat., 21, 155–167 (1970).
Scheffel et al.: J. Nucl. Med., 13, 498–503 (1972).

Primary Examiner—Richard D. Lovering

[57] ABSTRACT

A method is provided for incorporating water-soluble therapeutic agents in albumin microspheres. This method is particularly advantageous where the therapeutic agent is heat-sensitive. All steps of the method can be carried out at relatively low temperatures, such as ambient room temperature. The method may be applied to the preparation of intravascularly-administrable, magnetically-responsive microspheres.

4 Claims, No Drawings

METHOD OF INCORPORATING WATER-SOLUBLE HEAT-SENSITIVE THERAPEUTIC AGENTS IN ALBUMIN MICROSPHERES

CROSS-REFERENCE

This application is a continuation-in-part of copending application Ser. No. 820,812, filed Aug. 1, 1977, and now abandoned, which discloses but does not claim the subject matter of this application.

BACKGROUND AND PRIOR ART

In 1970, Zolle et al. reported the preparation of metabolizable radioactive human serum albumin microspheres. *Int. J. Appl. Radiat.*, 21, 155–167 (1970). The microspheres were prepared by dispersing droplets of a 25% solution of albumin in heated cottonseed oil with continuous stirring. Solidified microspheres were obtained after heating for 75 minutes at temperatures from 118° to 165° C. The microspheres were separated from the oil by centrifugation, washed free of oil with diethyl ether and dried in air. A similar procedure is described in Zolle U.S. Pat. No. 3,937,668 for incorporating precipitated drugs and other substances in albumin microspheres. According to the Zolle patent, it is necessary to heat the oil in which the microspheres are formed to a temperature above 100° C. to evaporate water and to form the spheric albumin particles having the precipitate encapsulated therein. Scheffel et al prepared albumin microspheres for study of the reticuloendothelial system using a modification of the Zolle procedure. Aqueous albumin was homogenized at room temperature with a small quantity of the oil, and the resulting emulsion was dispersed in a body of oil heated to 175°–185° C. with continuous stirring. On cooling, diethyl ether was added, the microcapsules recovered by centrifugation, washed with diethyl ether, and dried. Scheffel et al. *J. Nucl. Med.*, 13, 498–503 (1972). In 1974, Kramer proposed the use of a similar procedure for preparing albumin microspheres as vehicles for achieving specificity in drug delivery. Mercaptopurine was dissolved in the aqueous albumin prior to conversion to microspheres, and this water-soluble drug was shown to be entrapped in the microspheres. Kramer proposed that sonication could be used to produce smaller and more uniform size particles. Kramer, *J. Pharm. Sci.*, 63, 1646–1647 (1974).

SUMMARY OF INVENTION

Prior to the present invention, it was believed that in order to prepare recoverable albumin microspheres, one had to disperse the droplets of liquid aqueous albumin with the diagnostic or therapeutic agent in heated oil at temperatures of 100° C. or above, thereby forming the droplets into solid microspheres. This heating procedure evaporated water from the microspheres and denatured the albumin. This procedure was not usable for the encapsulation of heat-sensitive therapeutic agents. At temperatures of 100° C. or above, partial or complete inactivation of many important therapeutic agents will occur.

In the development of the present invention, it was discovered that albumin microspheres can be prepared without heating the aqueous albumin droplets. Even though water is not evaporated from the droplets and there is no denaturation of the albumin, water-soluble drugs can be entrapped in the microspheres, and the microspheres can be recovered for medical use or further processing. This discovery makes possible the preparation of microspheres containing water-soluble heat-sensitive therapeutic and/or diagnostic agents. As subsequently used herein the term "therapeutic agent" is intended to be inclusive of clinical agents which can be administered in microcapsular form, whether used primarily for treatment or diagnosis.

According to the method of the present invention, the aqueous albumin is dispersed and emulsified in a non-polar solvent (viz. a vegetable oil). The resulting water-in-oil emulsion containing droplets of the desired size can then be introduced into a body of the same solvent, such as vegetable oil, to further disperse the droplets. Neither the pre-formed emulsion or the body of vegetable oil are heated, ordinary room temperature or lower being satisfactory. The oil is removed by washing the dispersed droplets with an oil-soluble water-immiscible organic solvent, and the resulting microspheres are recovered in a portion of the organic solvent. Thereafter, the recovered microspheres can be dried, either with or without further treatment to harden the microspheres. The mechanism of formation of the microspheres is not fully understood. On the basis of prior knowledge, it is surprising that the microspheres as recovered do not coalesce but retain their structure as individual non-aggregated spheres.

DETAILED DESCRIPTION

The matrix material for forming the microspheres is albumin. Human serum albumin (HSA) is preferred. The albumin matrix material may be modified by using it in combination with a minor proportion of other biodegradable amino acid polymers. For example, from 0 to 25 parts by weight (dry basis) of hemoglobin (preferably human hemoglobin) or a synthetic amino acid polymer can be combined with 75–100 parts of albumin. Useable synthetic amino acid polymers include poly-L-lysine and poly-L-glutamic acid, having a molecular weight ranging from 20,000 to 50,000. Preferably, however, human serum albumin is employed as the sole matrix material.

In preparing the microspheres, an aqueous solution of the albumin matrix material is prepared, which can be formed into microspheres. The amount of matrix material to be used will usually be within the range from 5 to 50 parts by weight of the matrix material per 100 parts of water. Preferred proportions are from 20 to 30 parts per 100 parts of water. The water-soluble heat-sensitive therapeutic agent may be dissolved in the water of the matrix material solution, either before or after preparing the matrix solution.

The aqueous solution of the albumin matrix material containing the therapeutic agent is emulsified with an oil, which is preferably a vegetable oil, such as cottonseed oil, peanut oil, or the like. Other oil or suitable non-polar solvents for forming water-in-oil emulsions can be used. The aqueous phase at the time of addition of the oil may also contain the magnetic particles when previously added to the aqueous solution of the matrix material and dispersed therein. The proportions of the aqueous phase to the oil phase can conveniently range from about 1 to 5 parts by weight of the aqueous phase per 100 parts of the oil phase. This provides separation of the oil droplets, and prevents coalescence of the droplets in forming the microspheres. The water-in-oil emulsion is then treated to reduce the size of the dispersed droplets such as to an average size of below 3.0 microns. Procedures such as homogenization, or sonication, or both can be used. The resulting emulsion should be as homogeneous as possible. Where the microspheres are being prepared for intravascular administration, the completed emulsion should contain dispersed droplets of an average size of less than 1.5 microns, and preferably of an average size of less than 1.2 microns, corresponding to the desired size of the microspheres. If desired, an emulsifying agent may be used, but one is not needed and preferably is not used.

In one procedure, the emulsion is then added to a larger body of oil, which is preferably a vegetable oil, such as the same oil used to form the emulsion. In practice, cottonseed oil has been found to give good results. To promote the separation of the water droplets, the emulsion can be added in small increments to the oil bath, such as by dropwise addition. Preferably, also, the addition is accompanied by rapid stirring of the oil into which the emulsion is being introduced.

Alternatively, the aqueous albumin may be emulsified with the whole body of oil, such as by gradual or incremental addition of the oil to the albumin solution, using the droplet dispersion procedures referred to above.

For incorporation of the water-soluble heat-labile chemotherapeutic agents in the microspheres, it has been found that the process can be carried out without heating the oil, such as at essentially room temperature. In general, the body of oil into which the emulsion is introduced is maintained at a temperature at which there is no inactivation of the chemotherapeutic agent. Temperatures in the range of 1° to 45° C. are suitable, but it usually will not be necessary to either heat or cool the body of oil. For example, an essentially ambient room temperature, such as a temperature ranging from about 20° to 30° C. is advantageous.

It has been found that although there is no heat-denaturation of the albumin matrix material, the microspheres after introduction into the oil bath will maintain morphology and integrity as separate microspheres in a non-water miscible organic solvent, such as diethyl ether, ligroin, benzene, hexane, petroleum ether, and the like. The oil may be removed by washing with the organic solvent, such a diethyl ether, and the microspheres are recovered suspended in a portion of the organic solvent. If desired, the organic solvent can be removed by centrifugation and/or evaporation, and the resulting microspheres dried, preferably by lyophilization. The resulting product has a relatively rapid drug release rate in water or serum, but the lyophilized microspheres if not subjected to proteolytic enzyme action will continue to retain and release a water soluble agent over periods up to 48 hours.

Where a slower release rate is desired, and particularly where greater resistance to proteolytic enzyme degradation is needed, the microspheres after being formed and before drying can be treated with a cross-linking agent to increase its stability and decrease the drug release rate from the microspheres. Hardening of amino acid materials, such as albumin, as is known in the art, can be accomplished by treatment with a glyoxal or aldehyde. Specific reagents include dimethyl glyoxal, glyoxal, diphenyl glyoxal, formaldehyde, 2,3, butanedione, and similar aldehydes. For the purposes of the present invention, the glyoxal or aldehyde should be soluble in the organic solvent used to wash the microcapsules free of oil. For example, the organic solvent can contain a concentration of 0.2% to 20% by weight of the cross-linking agent, and may be contacted with the microspheres after or during the removal of the oil for from 5 to 120 minutes, depending on the degree of cross-linking desired. In general, the greater the amount of cross-linking, the slower will be the release rate for the water-soluble chemotherapeutic agent.

After completion of the cross-linking step, the microspheres can be washed free of excess cross-linking agent with a suitable organic solvent, as described above, such as diethyl ether, the residual solvent evaporated, and the microspheres dried, such as by lyophilization.

Formaldehyde is a particularly desirable cross-linking agent, but is generally available commercially only as a water solution. Such solutions contain from 4 to 37% by weight formaldehyde together with a small amount of methanol as a stabilizer. Although formaldehyde is preferentially water soluble, it can be transferred to an organic solvent, such as the solvents described above, by adding salt to the water solution. Ammonium sulfate can be used for this purpose at a concentration in the aqueous formaldehyde of about 60 to 80% by weight. The organic solvent containing the transferred formaldehyde can then be used for treating the microspheres to cross-link the matrix material.

The process of the present invention can be used for encapsulating any water-soluble therapeutic agent. As indicated, however, it is preferably applied to therapeutic agents which are heat-sensitive, and which would be damaged by prolonged heating, particularly heating at temperatures above 100° C. With many of such therapeutic agents, however, partial inactivation may occur at temperatures in the range of 50° to 100° C., and at those temperatures, at least partial denaturation of the albumin could be expected. Therefore, the process of the present invention is preferably carried out at a temperature in the range of 1° to 45° C., such as 20° to 30° C., or essentially ambient room temperature. The kinds of therapeutic agents which may be encapsulated include enzymes, chemotherapeutic agents, immunological adjuvants, and various natural products. Such water-soluble, heat-labile therapeutic agents include the following:

ENZYMES trypsinogen
chymotrypsinogen
plasminogen
streptokinase
adenyl cyclase
insulin
glucagon
coumarin
heparin
histamine

CHEMOTHERAPEUTIC AGENTS tetracycline
aminoglycosides
penicillin group of drugs, +Cephalosporins
sulfonamide drugs
chloramphenicol sodium succinate
erythromycin
vancomycin
lincomycin
clindamycin
nystatin
amphotericin B
amantidine idoxuridine
p-Amino salicyclic acid
isoniazid
rifampin
water-soluble alkylating agents in Ca therapy
water-soluble antimetabolites
antinomycin D
mithramycin
daunomycin, adriamycin
bleomycin
vinblastine
vincristine
L-asparaginase
procarbazine
imidazole carboxamide

IMMUNOLOGICAL ADJUVANTS concanavalin A
BCG
levamisole

NATURAL PRODUCTS prostaglandins, $PGE_1$, $PGE_2$
cyclic nucleotides
TAF antagonists
water-soluble hormones
lymphocyte inhibitors
lymphocyte stimulatory products The method of the present invention may be used to prepare magnetically-responsive microspheres. For this purpose, magnetic particles can be incorporated in the albumin solution together with the therapeutic agent for entrapment in the microspheres.

Usable magnetic particles include ferri- and ferromagnetic compounds, such as magnetic iron oxides. The preferred magnetic particles are the black oxide of iron, magnetite ($Fe_3O_4$). Carbonyl iron of appropriate size can be used instead of the $Fe_3O_4$. It is essential that the magnetic particles be in an ultra-fine state of subdivision. The magnetic particles should have an average size of not over 1,000 Ångstroms, and preferably not over 300 Ångstroms. The optimum size range for producing microcapsules of less than 1.5 microns average diameter (preferably less than 1.2 microns) is from about 50 to 250 Ångstroms.

Techniques are known for producing such extremely small size magnetic particles. These include fine grinding, vacuum deposition, and chemical precipitation. Fine grinding in a ball mill can be used to produce a colloidal suspension of magnetic particles. Commercially, fine powders or suspensions of $Fe_3O_4$ are available from Ferrofluidics Corporation, Burlington, Mass. The size range of the particles is from 100 to 200 Ångstroms. Aqueous base suspensions of the $Fe_3O_4$ particles with or without a surfactant can be used, but it is preferred to employ surfactant-free magnetic particles, such as $Fe_3O_4$ in a dispersed homogeneous suspension or in a dry powder form.

In practicing the present invention, from 5 to 350 parts by weight of the magnetic particles can be employed per 100 parts of the albumin matrix material (dry basis). This will result in microspheres containing corresponding proportions of the matrix material and magnetic particles. The preferred amount of magnetic material is from 10 to 150 parts by weight per 100 parts of the matrix material. The amount of the therapeutic agent can vary over a wide range, depending on the purpose for which the microspheres are to be used. However, in general, for water-soluble chemotherapeutic agents, from 1 to 20 parts by weight of the agent can be incorporated per 100 parts by weight of the matrix material. It will be understood, however, that the relative proportion of the therapeutic agent to the matrix material is not critical.

For further details, reference should be made to the following examples.

EXAMPLE I 125 mg human serum albumin, 10 mg bulk purified adriamycin HCl, and 36 mg $Fe_3O_4$ powder (200 Å average particle size) was placed in a 50 ml beaker and dissolved and suspended respectively in 0.5 ml distilled water. For experimental purposes, the albumin may be trace labeled with 0.1 mg $^{125}$I-bovine-serum-albumin. The suspension was stirred well to evenly disperse the $Fe_3O_4$ in the albumin-adriamycin solution, but no surfactant was employed to aid the dispersion. Next, 30 ml of cottonseed oil was added to the suspension forming a water-in-oil emulsion, which was then stirred well to disperse the aqueous phase into the oil.

The resultant emulsion was homogenized by sonication (Branson Sonifier Model 185) at 100 watts for one minute at 4° C. Next, the homogenate was added dropwise into 100 ml of cottonseed oil at 25° C. being constantly stirred at 1800 RPM for 10 minutes to fully disperse the emulsion.

The oil was then removed by washing 4 times in 60 ml diethyl ether anhydrous and centrifuged at 2000×g for 30 minutes. After the fourth wash the oil free microspheres were then hardened by a formaldehyde 1° w/v solution in 100 ml ether (8 mg microspheres/ml ether-formaldehyde solution). The ether-formaldehyde solution was prepared by transferring aqueous formaldehyde to the ether phase by shaking a 1:5 (37% aqueous-formaldehyde: ether) solution in the presence of saturating ammonium sulfate. The amount of formaldehyde transferred at this ratio was determined in a separate study using tritium labeled formaldehyde (1.5 mCi/1.5 mg) as a trace label in the 37% aqueous solution. The hardening was accomplished by dispersing the washed microspheres in the formaldehyde/ether and stirring at 100 RPM for the desired time (5 min to 2 hrs), depending on the extent of hardening desired. After hardening was terminated, the formaldehyde cross-linking reagent was removed by centrifugation in ether, four times. Any remaining ether was allowed to evaporate and the resultant material was further processed by lyophilization, and then stored at 4° C.

The microcapsule product contained approximately by weight 21% $Fe_3O_4$, 73% albumin, and 6% adriamycin. Examination by immersion fixation-transmission electron microscopy confirmed that the microcapsules were generally spherical in shape and of an average size of about 1 micron.

EXAMPLE II

Microspheres can be prepared by the procedure of Example I omitting the magnetic iron ($Fe_3O_4$), and incorporating other water-soluble therapeutic agents, such as any of those referred to above, instead of the adriamycin.

EXAMPLE III

The procedure for preparing the microspheres was identical to that of Example I except that 135 mg $Fe_3O_4$ was used instead of the 36 mg of Example I. The microcapsule product contained approximately by dry weight 50% $Fe_3O_4$, 4% adriamycin, and 46% albumin.

EXAMPLE IV

Microcapsules were prepared by the identical procedure of Example I, using approximately the same amount of $Fe_3O_4$ as in Example III. The $Fe_3O_4$ was in the form of an aqueous suspension containing a surfactant, aqueous base Ferrofluidics $Fe_3O_4$ Catalog No. A-01, 400 gauss saturation (Ferrofluidics Corporation, Burlington, Mass.). 0.3 ml of the A-01 product was added, containing approximately 130–140 mg $Fe_3O_4$. The average $Fe_3O_4$ particle size was in the range of 150–200 Ångstroms. The microcapsular product contained approximately by dry weight 51% $Fe_3O_4$, 4% adriamycin, and 45% albumin.

EXAMPLE V

A. Same procedure as Example I except microspheres are not hardened by a cross-linking agent. The oil bath is at a temperature of 20°–25° C. After the oil has been washed away with diethyl ether anhydrous 4 times, the spheres are separated from the remaining solvent, air dried, then lyophilized, and stored at 4° C.

Stability of the resultant microspheres was tested as follows: First, 5 microliters of $^{125}I$-bovine serum albumin (New England Nuclear, 1.51 mCi/mg) was added to the initial homogenate to trace label the microspheres. An aliquot of the resultant microspheres was then suspended and sonicated for 2 minutes in 0.154 M NaCl-0.1% Tween 80 and incubated at 37° C. for 24 and 48 hours. After this period of time, the suspension was centrifuged at 2000×g for 10 minutes and the supernatant and pellet were counted in a gamma counter. The number of counts obtained in the supernatant (after subtracting free label) divided by the total number of counts was regarded as the percentage breakdown of the carrier (non-pelleting). Only 16% of the microspheres had deteriorated after 24 hrs and 37% after 48 hrs. With formaldehyde or heat-hardening less than or equal to 3% deterioration occurs in 48 hrs.

B. Same procedure as Example I except 3,400 units of urokinase was added to the 125 mg of HSA omitting the $Fe_3O_4$ and adriamycin. No cross-linking was done in this experiment.

Two mg of the resultant microspheres were placed into 16 12×75 mm tubes of duplicate time course of 0, 15, 30, 60 minutes; 2, 4, and 6 hours. At the appropriate time, microspheres were suspended in sodium barbital buffer (0.05 M) and left at room temperature. Finally, at zero time all tubes were centrifuged at 3,500 RPM (1900×g) for 15 minutes at 4° C. and 25 microliters of the supernatants were pipetted into appropriate wells in fibrin-agar plates. Plates were then read 4 and 6 hours later for fibrinolysis (i.e. diameters).

It was found that 60% of maximum lysis was seen after 10 minutes on fibrin-agar plate.

OTHER EXAMPLES

As a variation of the procedure of the foregoing examples, butanedione (5% v/v in anhydrous ether) or butyraldehyde (10% v/v in anhydrous ether) is employed as a cross-linking agent, the contact time ranging from 5 minutes to 2 hours. The product can be recovered and dried as described in Example I.

As a further variation of the procedure for the foregoing examples, 20 mg of poly-L-lysine or polyglutamic acid is combined with the 125 mg of human serum albumin. The rest of the procedure is identical to Example I.

We claim:

1. The method of incorporating a water-soluble heat-sensitive therapeutic agent in albumin microspheres, in which all steps thereof are carried out at a temperature within the range from 1° to 45° C., said method including the steps of preparing an aqueous albumin solution of the said therapeutic agent, said albumin solution containing from 5 to 50 parts by weight of albumin per 100 parts of water and from 1 to 20 parts by weight of said therapeutic agent per 100 parts of albumin, emulsifying said albumin solution with a vegetable oil to form a water-in-oil emulsion containing dispersed droplets of the albumin solution, removing the oil by washing the dispersed droplets with an oil-soluble water-immiscible organic solvent, and recovering the resulting microspheres, wherein said method also includes the step of contacting said microspheres with an organic solvent solution of an aldehyde hardening agent to increase the stability of said microspheres and to decrease the release rate of said drug therefrom.

2. The method of claim 1 in which said hardening agent is formaldehyde, and in which said organic solvent solution is formed by transferring formaldehyde from an aqueous solution thereof into said organic solvent, the residual aqueous solution being separated from said organic solvent solution prior to said contacting.

3. The method of claim 1 or claim 2 in which said albumin solution also contains magnetic particles.

4. The method of claim 13 or claim 2 in which said organic solvent solution contains from 0.2 to 20% by weight of said aldehyde hardening agent.

* * * * *